(12) United States Patent
Beddar et al.

(10) Patent No.: US 9,907,980 B2
(45) Date of Patent: Mar. 6, 2018

(54) REAL-TIME IN VIVO RADIATION DOSIMETRY USING SCINTILLATION DETECTOR

(71) Applicant: THE BOARD OF REGENTS OF THE UNIVERSITY OF TEXAS SYSTEM, Austin, TX (US)

(72) Inventors: A. Sam Beddar, Houston, TX (US); Tina Marie Briere, Houston, TX (US); Louis Archambault, Québec (CA)

(73) Assignee: Board of Regents, The University of Texas System, Austin, TX (US)

(*) Notice: Subject to any disclaimer, the term of this patent is extended or adjusted under 35 U.S.C. 154(b) by 34 days.

(21) Appl. No.: 14/251,796

(22) Filed: Apr. 14, 2014

(65) Prior Publication Data

US 2014/0221724 A1 Aug. 7, 2014

Related U.S. Application Data

(63) Continuation of application No. 13/143,567, filed as application No. PCT/US2010/020366 on Jan. 7, 2010, now Pat. No. 8,735,828.

(60) Provisional application No. 61/143,294, filed on Jan. 8, 2009.

(51) Int. Cl.
*G01T 1/20* (2006.01)
*A61N 5/10* (2006.01)
*G01T 1/161* (2006.01)
*G01T 1/02* (2006.01)

(52) U.S. Cl.
CPC ......... *A61N 5/1071* (2013.01); *A61N 5/1048* (2013.01); *G01T 1/023* (2013.01); *G01T 1/161* (2013.01); *A61N 2005/1072* (2013.01)

(58) Field of Classification Search
CPC .......... G01T 1/023; A61M 2025/1013; A61M 2025/1047; A61M 2025/1068; A61M 25/104; A61M 25/1002
USPC .... 250/370.11, 362, 368; 600/407, 431, 436
See application file for complete search history.

(56) References Cited

U.S. PATENT DOCUMENTS

| | | | |
|---|---|---|---|
| 4,976,266 A | 12/1990 | Huffman et al. | |
| 5,325,855 A | 7/1994 | Daghighian et al. | |
| 5,476,095 A * | 12/1995 | Schnall | A61B 5/055 600/423 |
| 5,811,814 A * | 9/1998 | Leone | A61B 6/4258 250/368 |
| 6,061,644 A * | 5/2000 | Leis | G01S 5/163 382/103 |
| 6,295,680 B1 * | 10/2001 | Wahl | A61B 6/425 600/431 |

(Continued)

FOREIGN PATENT DOCUMENTS

WO WO 01/49162 7/2001

OTHER PUBLICATIONS

Archambault et al., "Measurement accuracy and Cerenkov removal for high performance, high spatial resolution scintillation dosimetry," Med. Phys., 33(1):128-135, 2006.

(Continued)

*Primary Examiner* — David Porta
*Assistant Examiner* — Djura Malevic
(74) *Attorney, Agent, or Firm* — Parker Highlander PLLC

(57) ABSTRACT

Apparatus and methods for measuring radiation levels in vivo in real time. Apparatus and methods include a scintillating material coupled to a retention member.

13 Claims, 13 Drawing Sheets

(56) References Cited

U.S. PATENT DOCUMENTS

| | | | | |
|---|---|---|---|---|
| 6,547,788 B1* | 4/2003 | Maguire | ............... | A61B 18/00 |
| | | | | 606/41 |
| 6,649,914 B1* | 11/2003 | Moorman | ............... | A61B 6/06 |
| | | | | 250/363.06 |
| 6,746,465 B2* | 6/2004 | Diederich | ............. | A61M 29/02 |
| | | | | 604/101.02 |
| 6,782,289 B1 | 8/2004 | Strauss | | |
| 6,963,771 B2* | 11/2005 | Scarantino | ............ | A61B 5/0031 |
| | | | | 128/903 |
| 7,204,796 B1* | 4/2007 | Seiler | ........................ | A61B 5/06 |
| | | | | 600/3 |
| 7,328,058 B2* | 2/2008 | Iwanczyk | ............ | A61B 6/4057 |
| | | | | 600/425 |
| 7,361,134 B2* | 4/2008 | Rozenfeld | ............ | A61N 5/1007 |
| | | | | 600/1 |
| 7,491,942 B2* | 2/2009 | Black | ................... | A61N 5/1048 |
| | | | | 250/370.07 |
| 7,662,083 B2* | 2/2010 | Gueye | ................. | A61N 5/1027 |
| | | | | 600/7 |
| 7,976,497 B2* | 7/2011 | Shah | ................. | A61M 25/1002 |
| | | | | 604/103.06 |
| 8,080,031 B2* | 12/2011 | Isham | ............... | A61M 25/1002 |
| | | | | 604/103.06 |
| 8,133,167 B2* | 3/2012 | Gueye | ................... | A61N 5/1027 |
| | | | | 600/7 |
| 8,183,534 B2* | 5/2012 | Lacroix | ..................... | G01T 1/02 |
| | | | | 250/370.07 |
| 8,241,317 B2* | 8/2012 | Isham | ................... | A61M 29/02 |
| | | | | 606/192 |
| 8,454,648 B1* | 6/2013 | Isham | ................... | A61M 29/00 |
| | | | | 128/DIG. 26 |
| 8,568,285 B2* | 10/2013 | Keppel | .................... | G01T 1/205 |
| | | | | 600/7 |
| 9,028,390 B2 | 5/2015 | Keppel et al. | | |
| 2001/0011174 A1* | 8/2001 | Reiley | ................. | A61B 17/7097 |
| | | | | 606/86 R |
| 2002/0022799 A1* | 2/2002 | Apple | ................... | A61N 5/1002 |
| | | | | 604/96.01 |
| 2002/0114829 A1* | 8/2002 | Onyuksel | ............. | A61K 9/1271 |
| | | | | 424/450 |
| 2003/0028097 A1* | 2/2003 | D'Amico et al. | ...... | A61B 5/055 |
| | | | | 600/427 |
| 2003/0028211 A1* | 2/2003 | Crocker | .................... | A61F 2/86 |
| | | | | 606/192 |
| 2003/0114744 A1* | 6/2003 | Pantages | ................... | A61B 8/12 |
| | | | | 600/407 |
| 2004/0116807 A1* | 6/2004 | Amrami | ................... | A61B 6/00 |
| | | | | 600/436 |
| 2005/0010110 A1* | 1/2005 | Black | ................... | A61N 5/1048 |
| | | | | 600/436 |
| 2005/0012043 A1* | 1/2005 | Motomura | ............ | A61B 6/4258 |
| | | | | 250/363.01 |
| 2005/0209548 A1* | 9/2005 | Dev | ........................ | A61N 1/306 |
| | | | | 604/20 |
| 2006/0058681 A1* | 3/2006 | Eberle | ........................ | A61B 8/06 |
| | | | | 600/466 |
| 2006/0178577 A1* | 8/2006 | Iwanczyk | ............ | A61B 6/4057 |
| | | | | 600/425 |
| 2007/0016071 A1* | 1/2007 | Eberle | ........................ | A61B 8/06 |
| | | | | 600/468 |
| 2007/0032862 A1* | 2/2007 | Weber | ........................ | A61F 2/82 |
| | | | | 623/1.34 |
| 2007/0038061 A1* | 2/2007 | Huennekens | .......... | A61B 6/504 |
| | | | | 600/407 |
| 2007/0114425 A1 | 5/2007 | Wong et al. | | |
| 2007/0129693 A1 | 6/2007 | Hemond et al. | | |
| 2009/0018393 A1* | 1/2009 | Dick | ..................... | A61B 5/0062 |
| | | | | 600/109 |
| 2009/0030258 A1* | 1/2009 | Axelrod | ............ | A61M 25/1002 |
| | | | | 600/4 |
| 2009/0121144 A1* | 5/2009 | Black | ................... | A61N 5/1048 |
| | | | | 250/370.07 |
| 2009/0248049 A1* | 10/2009 | Perkins | .............. | A61B 17/3478 |
| | | | | 606/159 |
| 2010/0081933 A1* | 4/2010 | Sverdlik | .............. | A61B 5/0048 |
| | | | | 600/439 |
| 2010/0145379 A1* | 6/2010 | Isham | .................... | A61B 5/411 |
| | | | | 606/192 |
| 2010/0217119 A1* | 8/2010 | Forster | ................. | A61B 5/0536 |
| | | | | 600/425 |
| 2010/0288934 A1* | 11/2010 | Keppel | .................... | G01T 1/205 |
| | | | | 250/362 |
| 2011/0137124 A1* | 6/2011 | Milner | ................. | A61B 5/0062 |
| | | | | 600/160 |
| 2012/0078177 A1* | 3/2012 | Isham | ............... | A61M 25/1002 |
| | | | | 604/103.08 |

OTHER PUBLICATIONS

Archambault et al., "Plastic scintillation dosimetry: optimal selection of scintillating fibers and scintillators," *Med. Phys.*, 32(7):2271-2278, 2005.

Beddar et al., "A miniature "scintillator-fiberoptic-PMT" detector system for the dosimetry of small fields in stereotactic radiosurgery," *IEEE Transactions on Nuclear Science*, 48(3):924-928, 2001.

Beddar et al., "Cerenkov light generated in optical fibres and other light pipes irradiated by electron beams," *Phys. Med. Biol.*, 37(4):925-935, 1992.

Beddar et al., "Plastic scintillation dosimetry for radiation therapy: minimizing capture of Cerenkov radiation noise," *Phys. Med. Biol.*, 49:783-790, 2004.

Beddar et al., "Plastic scintillation dosimetry: optimization of light collection efficiency," *Phys. Med. Biol.*, 48:1141-1152, 2003.

Das et al., "Characteristics of a scintillator-based daily quality assurance device for radiation oncology beams," *Med. Phys.*, 23(12):2061-2067, 1996.

De Boer, "Optical filtering and spectral measurements of radiation-induced light in plastic scintillation dosimetry," *Phys. Med. Biol.*, 38:945-958, 1993.

Essers and Mijnheer, "In Vivo dosimetry during external photon beam radiotherapy," *Int. J. Radiation Oncology Biol. Phys.*, 43(2):245-259, 1999.

Fiorino et al., "Quality assurance by systematic in vivo dosimetry: results on a large cohort of patients," *Radiotherapy and Oncology*, 56:85-95, 2000.

Ikhlef et al., "X-ray imaging and detection using plastic scintillating fibers," *Nuclear Instruments and Methods in Physics Research A.*, 442:428-432, 2000.

Jordan, "Evaluation of ruby as a fluorescent sensor for optical fiber-based radiation dosimetry," *SPIE*, 2705:170-178, 1996.

Létourneau et al., "Miniature scintillating detector for small field radiation therapy," *Med. Phys.*, 26(12):2555-2561, 1999.

Macri et al., "Readout of scintillating plastic fibers with an APD array and prototype ASIC," IEEE Transactions on Nuclear Science, 50(4):928-935, 2003.

Aznar et al., "A Monte Carlo study of the energy dependence of AI203:C crystals for real-time in vivo dosimetry in mammography", *Radiat Prot Dosimetry*, 114:444-449, 2005.

Aznar et al., "Real-time optical-fibre luminescence dosimetry for radiotherapy: physical characteristics and applications in photon beams", *Phys Med Biol.*, 49:1655-1669, 2005.

Beddar et al., "Absorbed dose perturbation caused by diodes for small field photon dosimetry", *Med Phys.*, 21:1075-1079, 1994.

Beddar et al., "Monte Carlo calculations of the absorbed dose and energy dependence of plastic scintillators", *Med. Phys.*, 32:1265-1269, 2005.

Beddar et al., "Preliminary evaluation of implantable MOSFET radiation dosimeters", *Phys Med Biol.*, 50:141-149, 2005.

Beddar et al., "Water-equivalent plastic scintillation detectors for high-energy beam dosimetry: I. Physical characteristics and theoretical consideration", *Phys Med Biol.*, 37:1883-1900, 1992.

Beddar et al., "Water-equivalent plastic scintillation detectors for high-energy beam dosimetry: II. Properties and measurements", *Phys Med Biol.*, 37:1901-1913, 1992.

(56) References Cited

OTHER PUBLICATIONS

Office Action issued in U.S. Appl. No. 13/143,567, dated Aug. 16, 2013.
PCT International Preliminary Report on Patentability issued in International Application No. PCT/US2010/020366, dated Jul. 12, 2011.
PCT International Search Report and Written Opinion issued in International Application No. PCT/US2010/020366, dated Aug. 25, 2010.
Ramaseshan et al., "Performance characteristics of microMOSFET as an in vivo dosimeter in radiation therapy", *Phys Med Biol.*, 49:4031-4048, 2004.
Scarantino et at., "An implantable radiation dosimeter for use in external bam radiation therapy", *Med Phys.*, 31:2658-2671, 2004.
Soubra and Cygler, "Evaluation of a dual bias dual metal oxide-silicon semiconductor field effect transistor detector as radiation dosimeter", *Med Phys.*, 21:567-572, 1994.
"Exradin® W1 Scintillator," Standard Imaging Inc., located at www.standardimaging.com/exradin/exradin-scintillator, 2017.
"Water-equivalent plastic scintillation dectors for small-field radiotherapy," Standard Imaging, Inc., SBIR grant information, 2010.
"Water-equivalent plastic scintillation dectors for small-field radiotherapy," Standard Imaging, Inc., SBIR grant information, 2013.
"Water-equivalent plastic scintillation dectors for small-field radiotherapy," Standard Imaging, Inc., SBIR grant information, Period of Performance Aug. 1, 2013-Jul. 31, 2014, 2017.
"Water-equivalent plastic scintillation dectors for small-field radiotherapy," Standard Imaging, Inc., SBIR grant information, Period of Performance Aug. 1, 2014-Jul. 31, 2015, 2017.
Alsanea et al.,"SU-E-T-486: in vivo skin dosimetry using the exradin W1 plastic scintillation detector for passively scattered proton beam therapy," *Medical Physics*, 42(6):3446, 2015. Abstract.
Bourgouin et al., "Characterization and validation of a commercial plastic scintillation detector prototype: exradin W1 scintillator," Poster No. E31-1099, 2012.
Carrasco et al.,"Characterization of the exradin W1 scintillator for use in radiotherapy," *Mod. Phys.*, 42(0:297-304, 2015.
Fontbonne et al., "Scintillating fiber dosimeter for radiation therapy accelerator," *IEEE Transactions on Nuclear Science*, 49(5):2223-2227, 2002.
Frelin et al.,"Sepctral discrimination of Cerenkov radiation in scintillating dosimeters," *Med. Phys.*, 32(9):3000-3006, 2005.
Letter to Radiadyne, from ZModDynamics, dated Apr. 6, 2017.
Pino et al.,"Su-E-T-423: TrueBeamsmall field dosimetry using commercial plastic scintillation and other stereotactic detectors," *Medical Physics*, 41(6):323, 2014. Abstract.
Pino et al.,"TrueBeam small field dosimetry using commercial plastic scintillation and other stereotactic detectors," Presentation, 2014.

\* cited by examiner

REAL-TIME IN VIVO RADIATION DOSIMETRY USING SCINTILLATION DETECTOR

The present application is a continuation application of U.S. Ser. No. 13/143,567, filed Dec. 2, 2011, which is national phase application under 35 U.S.C. §371 of international application Serial No. PCT/US2010/020366, filed Jan. 7, 2010, which claims benefit of priority to U.S. provisional application Ser. No. 61/143,294, filed Jan. 8, 2009, the entire contents of which are hereby incorporated by reference.

BACKGROUND OF THE INVENTION

1. Field of the Invention

The present invention relates generally to the fields of radiation dosimetry. More particularly, it concerns the use of scintillating detectors to detect radiation levels in vivo.

2. Description of Related Art

Cancer recurrence is frequently the result of failed local control of treatment options. Reducing the likelihood of recurrence in radiotherapy means giving the largest possible radiation dose to the tumor region while limiting the dose to healthy organs at risk for treatment-induced toxicity. Even with the best treatment planning modalities, there is no guarantee that the prescribed dose will be delivered exactly as planned. Internal movements such as breathing or uncertainties in the filling of organs such as the bladder and rectum may displace the target volume away from the intended treatment field. At the same time, normal tissues may be shifted into the high dose region, introducing unnecessary radiation-induced side effects. The use of in vivo dosimetry to monitor the actual dose received in the target or healthy tissue is the best way to ensure accurate dose delivery. Accurate in vivo dosimetry is an important step towards measuring the dose to the organs at risk in order to assess the quality of the treatment, maximize the dose to the tumor and/or minimize the risk of complications to normal tissues. Presently there are no known available in vivo dosimetry systems that can sample both dose and dose rate fast enough to be suitable for real-time feedback.

With the advent of intensity modulated radiotherapy (IMRT) and conformal proton radiotherapy, there now exists the ability to create a treatment plan with margins small enough to target the tumor while largely sparing the healthy tissues and organs at risk. CT-Linac-based image-guided radiotherapy (IGRT), cone-beam CT and on-board imaging (OBI) systems allows a user to accurately set up a patient relative to the treatment beams just prior to treatment. However, there is no guarantee that the target will remain in the same place during the entire treatment period. Even with the use of increasingly sophisticated radiotherapy techniques, it is difficult to determine if the dose has been delivered exactly as planned. And, if not, it can be difficult to determine the degree to which the actual dose has deviated from the planned dose.

Precise measurement of the dose to organs at risk and other critical structures is therefore necessary to provide a clear picture of the true dose delivered during any given treatment fraction. The benefits of such measurements are multi-fold. First, comparison of the measured dose to that planned will indicate deviations in set up and/or anatomy that indicate the need for changes in the treatment plan. Second, consideration of tumor control and the probability of normal tissue complications will allow a radiation oncologist to either escalate or reduce the dose over the course of a radiotherapy treatment. Finally, knowledge of the true delivered dose will allow for more accurate analysis of organ toxicity. The benefits to the patients will include decreased likelihood of local failure and reduced frequency of life-altering side effects.

The main radiation dosimeters available at the present time include thermoluminescent detectors (TLDs), ionization chambers, radiographic film, silicon (Si) diodes and metal-oxide semiconductor field effect transistor (MOSFET) devices. None of these detectors, aside from Si diodes, allows real-time measurement of dose rate, and none are water equivalent. TLDs, ionization chambers and film do not allow in vivo dose measurements for various reasons (too bulky, slow response, safety concerns, etc.). Even though Si diodes may have good spatial resolution, they suffer from strong energy dependence and are prone to dose perturbation depending on their orientation with respect to the beam (Beddar et al. 1994).

MOSFETs have been commercialized for in vivo dosimetry. Although some systems offer unique advantages including the ability to be permanently implanted and read telemetrically, MOSFETs tend to show angular dependence, energy dependence, and a decreased sensitivity with increasing absorbed dose, requiring either in-house or factory calibration (Soubra et al. 1994; Scarantino et al. 2004; Ramaseshan et al. 2004; Beddar et al. 2005). MOSFET detectors also have a limited lifetime of 70-200 Gy.

Preliminary studies of optically stimulated luminescence (OSL) devices do show promise (Aznar et al. 2004; Aznar et al. 2005). The devices produce spontaneous emission due to radio-luminescence, which exhibits a non-linear dependence with dose rate, as well as optically stimulated luminescence, which can be integrated to obtain the total accumulated dose.

Although these devices can be used for in vivo dose measurements, they suffer from other drawbacks. These include their non-water-equivalence and the required time delay of 5 to 6 minutes needed to retrieve the dose data between measurements. This occurs because the OSL signal related to absorbed dose arises from electron traps that must be optically stimulated with a laser. Thus, one could not use these detectors to discriminate between individual beams in an IMRT or even a two-field proton therapy treatment.

It is clear that none of the detectors described above would satisfy the needs of the real-time in vivo dosimetry that would provide feedback fast enough to enable adaptive radiotherapy. Only plastic scintillators can be used to measure both dose and dose rate in real time. Plastic scintillators have been shown to be water equivalent (Beddar, et. al 1992), linear with dose, dose rate independent, energy independent in the megavoltage energy range, and unaffected by changes in temperature. Moreover the light emission mechanism of a plastic scintillator is fast (nanoseconds) and therefore well suited for real-time applications. So far, several prototypes of plastic scintillation detectors have been proposed for applications in quality assurance, stereotactic radiosurgery, brachytherapy and general dosimetry but no scintillation detector to date can achieve real-time in vivo dosimetry.

A multiple-probe scintillation detector system has been recently developed for quality assurance but can only be used in phantom and not in patients. Moreover the design of this detector system requires an acquisition time that is at least as a long as a radiotherapy treatment fraction, this design flaw prevents any real-time applications.

SUMMARY OF THE INVENTION

Delivering the correct dose to the intended area is the most basic goal of any radiotherapy treatment. The most direct way to confirm the true dose delivered to a location of interest is to measure that dose in situ. In prostate radiotherapy, the outcome (biochemical and local control) depends on accurate delivery of the dose to the prostate as planned. At the same time, it is important to ensure that the tolerance to critical structures (rectum, urethra, and erectile tissues) is within acceptable limits so that toxicity is minimized and quality of life is not compromised.

It is believed that direct measurement of the dose delivered to organs, critical structures, and within the vicinity of a tumor is feasible and can be used to verify treatment plan delivery. It is also believed that this can be done using an in vivo scintillation detector composed of multiple probes arranged in an application-specific design that can monitor true in vivo dose in real time.

Plastic scintillation detectors are constructed from three main components: a miniature scintillating material that luminesces (emits visible light) when irradiated, an optical guide that carries the light, and a photodetector that converts the light into a measurable signal. In certain embodiments, sub-millimeter diameter scintillating fibers will be used for their spatial resolution as well as their flexibility, allowing them to conform to the curvatures of internal anatomy.

Objectives include the ability to: a) establish the dosimetric characteristics and properties of scintillating fibers in photon and proton radiotherapy beams as well as an Ir-192 HDR brachytherapy source, b) design, construct, and test detector systems for rectal and urethral in vivo applications, and c) measure the dose to the rectal wall and urethra for a small cohort of patients.

Successful implementation of the disclosed systems and methods will allow for monitoring the true dose delivered to organs and other tissues at risk during radiotherapy. This method can be used to generate data to assess the dose to the organs and critical structures and can be used to maximize the dose to the tumor and/or minimize the risk of complications to normal tissue. The resulting data can also be used to study dose-related treatment side effects. The ultimate goal of utilizing this method is to improve the delivery of radiotherapy treatments and the quality of life of radiotherapy patients.

Certain embodiments of the present disclosure comprise an apparatus configured to measure radiation levels in vivo. In specific embodiments, the apparatus comprises: a retention member configured to retain the apparatus in a location in vivo; a scintillating material configured to emit light when irradiated; an optical guide configured to transport light emitted from the scintillating material; and a photodetector configured to detect light emitted from the scintillating material and transported by the optical guide.

In particular embodiments, the retention member is inflatable. The apparatus may further comprise a data analyzer configured to analyze an output from the photodetector. The scintillating material may be configured as an optical fiber in certain embodiments. The scintillating material may be coupled to the retention member in particular embodiments. The scintillating material may be wrapped around the retention member to form a spiral about a primary axis of the retention member to provide information about a radiation dose delivered to the all or part of the surface of the retention member. In other embodiments, the scintillating material may be wrapped around the retention member to form an annular arrangement about a primary axis of the retention member. In certain embodiments, the scintillating material is arranged parallel to a primary axis of the retention member.

The scintillating material may be formed as a plurality of optical fibers arranged parallel to a primary axis of the retention member and extending and wherein one or more of the optical fibers extend different lengths along the retention member. Particular embodiments may further comprise radiopaque markers coupled to the retention member. In certain embodiments, the radiopaque markers can be embedded in the retention member. In particular embodiments, the radiopaque markers are configured parallel or perpendicular to a primary axis of the retention member.

In certain embodiments, the retention member is configured as an inflatable balloon with an external shape that conforms to a prostate of a patient. In specific embodiments, the retention member has a cross-section that is generally elliptical and has a greater width than height and comprises an indentation along the width. In particular embodiments, the retention member comprises an insertion rod coupled to a plurality of radiopaque markers and the scintillating material. In certain embodiments, the retention member comprises a flexible coupling member coupled to a plurality of detectors comprising scintillating material. In certain embodiments, the retention member comprises a flexible coupling member coupled to a plurality of radiopaque markers. In particular embodiments, the retention member is configured as a rigid probe. Certain embodiments may further comprise a plurality of radiopaque markers and a plurality of detectors comprising scintillating material.

In particular embodiments, the scintillating material comprises a wavelength shifting member. In specific embodiments, the retention member may be an ultrasonic probe.

Certain embodiments may also comprise a method of measuring radiation levels in vivo. The method may comprise: providing a scintillating material, wherein the scintillating material is configured to emit light when exposed to radiation; coupling the scintillating material to a retention member; securing the retention member in a specific location in vivo; exposing the specific location and the scintillating material to radiation; measuring the amount of light emitted from the scintillating material; and calculating the level of radiation at the specific location based on the amount of light emitted from the scintillating material.

In certain embodiments, securing the retention member to the specific location in vivo comprises inflating the retention member. In particular embodiments, coupling the scintillating material to the retention member comprises coupling the scintillating material to a cover and placing the cover over the retention member. Coupling the scintillating material to the retention member may also comprise inserting the scintillating material into a channel of the retention member.

In particular embodiments, coupling the scintillating material to the retention member comprises wrapping the scintillating material around the retention member. The scintillating material can be configured as one or more fibers, and coupling the scintillating material to the retention member may comprise arranging the or more fibers in an annular or a spiral arrangement about a primary axis of the retention member.

In particular embodiments, calculating the level of radiation at the specific location based on the amount of light emitted from the scintillating material is performed in real time. In certain embodiments, measuring the amount of light emitted from the scintillating material comprises transferring light from the scintillating material to a photodetector via an optical coupling and a fiber light guide.

Particular embodiments comprise measuring the amount of light emitted from the scintillating material by transferring light emitted from the scintillating material to a wavelength shifting member.

Certain embodiments comprise comparing the calculated level of radiation at the specific location to a predetermined level of radiation. Particular embodiments further comprise automatically stopping the exposure of radiation when the level of calculated level of radiation at the specific location is equal to the predetermined level of radiation.

Certain embodiments comprise providing one or more radiopaque markers coupled to the retention member, where the one or more radiopaque markers are configured to be visible when the retention member is exposed to radiation in vivo. In particular embodiments, the one or more radiopaque markers extend parallel to a primary axis of the retention member. In certain embodiments, the one or more radiopaque markers extend perpendicular to a primary axis of the retention member. In specific embodiments, the one or more radiopaque markers are configured to allow the longitudinal and rotational position of the retention member to be determined when the retention member is exposed to radiation in vivo.

The terms "a" and "an" are defined as one or more unless this disclosure explicitly requires otherwise.

The term "approximately" and its variations are defined as being close to as understood by one of ordinary skill in the art, and in one non-limiting embodiment the terms are defined to be within 10%, preferably within 5%, more preferably within 1%, and most preferably within 0.5%.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The term "coupled," as used herein, is defined as connected, although not necessarily directly, and not necessarily mechanically.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
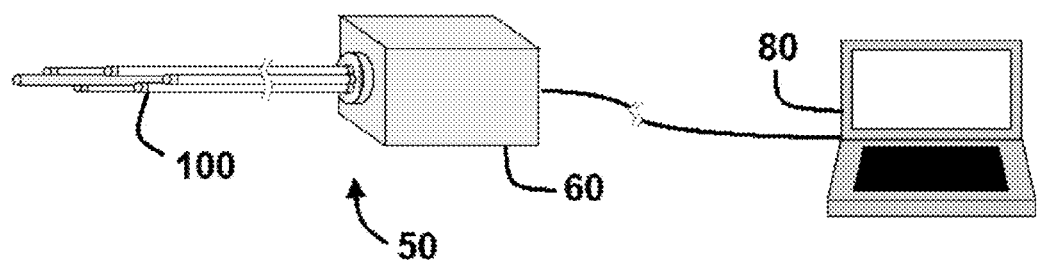
FIG. 1 illustrates a perspective view of an exemplary embodiment of a detector system according to the present disclosure.

Referring initially to FIG. 1, an exemplary embodiment of a detector system 50 is configured to measure in vivo and in real time the amount of radiation delivered to a specific location within a patient's body. In this exemplary embodiment, detector system 50 comprises one or more detectors 100 configured to detect radiation, a CCD camera 60, and a data analyzer 80 (e.g., a computer) configured to analyze the radiation levels detected by the detectors 100. Other devices may be substituted for the CCD camera, including a CMOS detector, photmultiplier tube (PMT) array, photodiodes and/or avalanche photodiodes (APD).

As explained in more detail below, during operation the one or more detectors 100 may be coupled to a retention member that retains the detectors in a desired location within a patient. The patient may then be exposed to radiation (e.g., as part of radiation therapy for cancer) in the location where the detectors have been placed.

Figure 2:
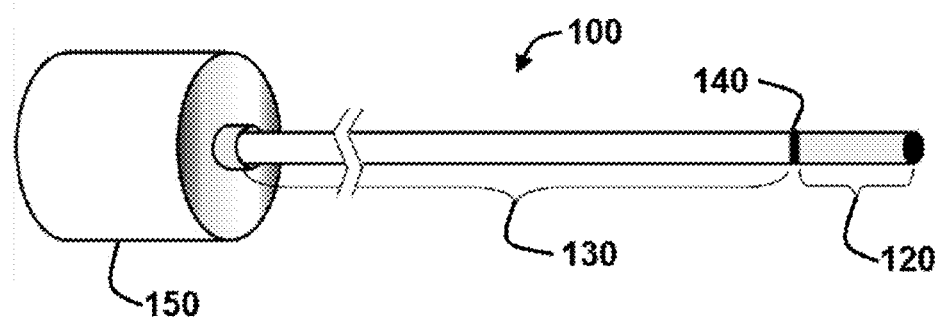
FIG. 2 illustrates a perspective view of an exemplary embodiment of a detector according to the present disclosure.

Referring now to FIG. 2, a more detailed view of a detector 100 illustrates the detector comprises a scintillating material 120 configured to emit light when irradiated. In certain embodiments, scintillating material 120 may be relatively short (e.g. approximately 1, 2, 3, 4 or 5 mm long) to measure radiation dose to a specific point. In certain embodiments, scintillating material 120 may be longer (e.g. approximately 20, 30, 40, 50, 60, 70, 80, 90 or 100 mm long) to measure radiation dose to a specific length or area. In certain embodiments, scintillating material 120 may be configured as one or more scintillating fibers. In the embodiment shown, scintillating material 120 is coupled to an optical fiber light guide 130 via an optical coupling 140, which is in turn coupled to a photodetector 150. During use, scintillating material 120 will therefore emit a light when exposed to a sufficient level of radiation. This light will be transferred from scintillating material 120 to photodetector 150 via optical coupling 140 and fiber light guide 130. Photodetector 150 (and the associated data analyzer) can then determine which detectors are emitting light, and consequently, which areas have been exposed to a threshold level of radiation.

Figure 3:
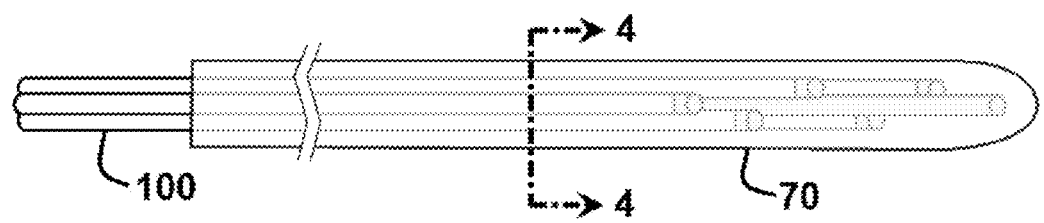
FIG. 3 illustrates a side view of an exemplary embodiment of a retention member and a plurality of detectors, according to the present disclosure.

As shown in the exemplary embodiment of FIG. 3, a plurality of detectors 100 can be coupled to a retention member 70. Retention member 70 may be used to hold detectors 100 in a desired location during radiation treatment. In specific embodiments, retention member 70 may comprise an inflatable portion so that it may be inserted into the patient while deflated and then inflated to increase its size when it is in the desired location. This can allow the retention member to remain in a specific location during radiation treatment and provide for more accurate detection of radiation levels.

Figure 4A:
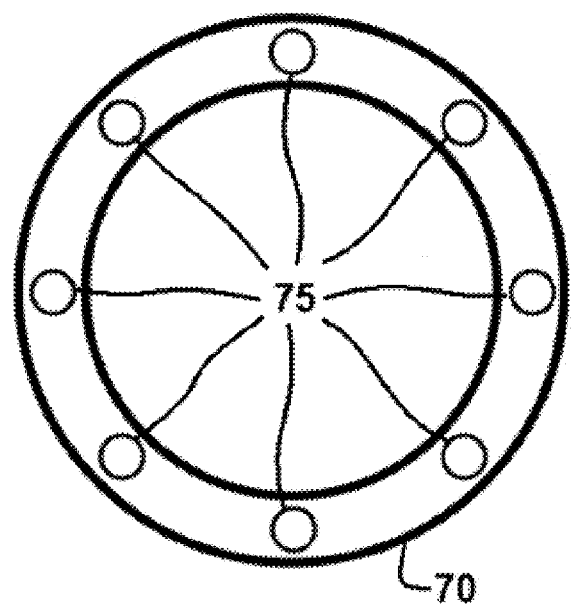
FIG. 4A illustrates a section view taken along line 4-4 of the exemplary embodiment illustrated in FIG. 3.

In certain embodiments, detectors 100 may be coupled to retention member 70 via channels within retention member 70. As shown in the section view of FIG. 4A taken along line 4-4 of FIG. 3, channels 75 may be integral to retention member 70 and distributed around the circumference of retention member 70. In this embodiment, a detector 100 can be inserted into each channel 75 so that the radiation levels can be detected around the circumference of retention member 70.

Figure 4B:
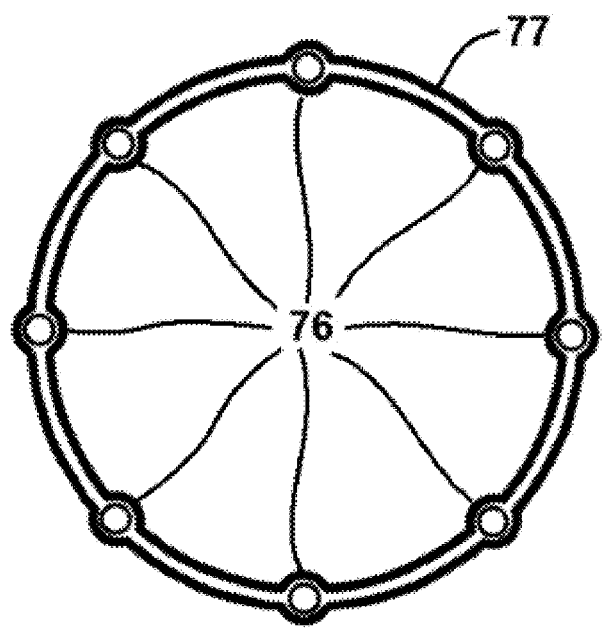
FIG. 4B illustrates a section view taken along line 4-4 of the exemplary embodiment illustrated in FIG. 3.

In other embodiments, detectors 100 may be coupled to retention member 70 via a cover that fits over retention member 70. As shown in the section view of FIG. 4B, detectors 100 may be inserted into channels 76 of a cover 77 that may be disposed over a retention member. In certain embodiments, cover 77 and/or retention member 70 may be disposable components, while detectors 100 (which are contained within channels 75 or 76) are sterilized and re-used.

Figure 5:
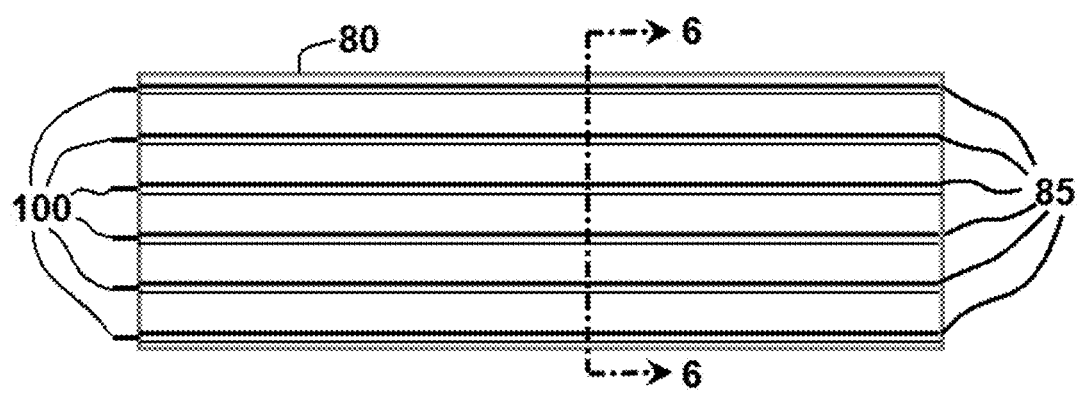
FIG. 5 illustrates a side view of an exemplary embodiment of a cover and a plurality of detectors, according to the present disclosure.
Figure 6:
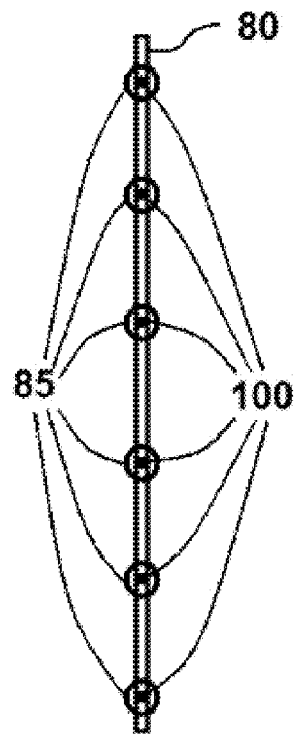
FIG. 6 illustrates a section view taken along line 6-6 of the exemplary embodiment illustrated in FIG. 5.
Figure 7:
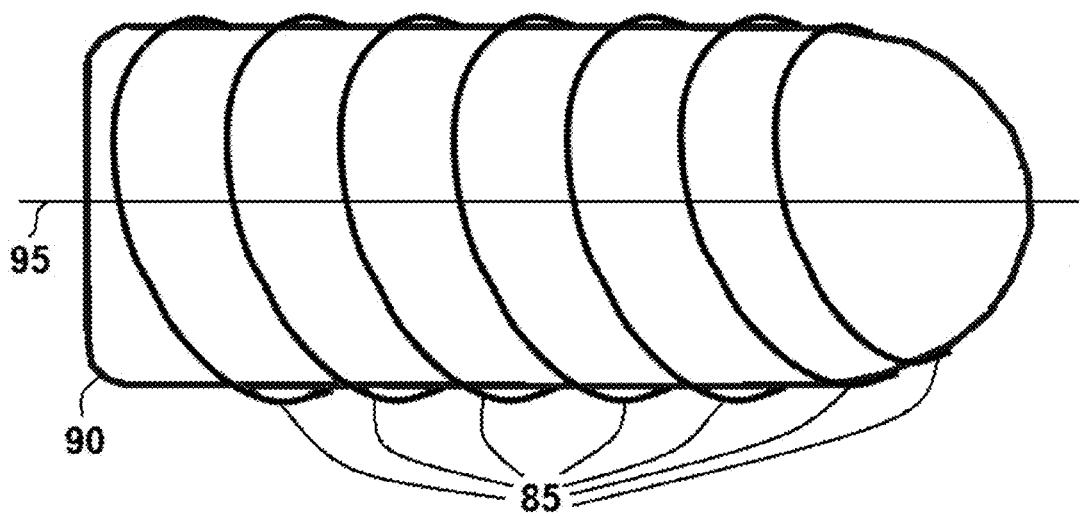
FIG. 7 illustrates a perspective view of an exemplary embodiment of a retention member and a plurality of detectors, according to the present disclosure.
Figure 8:
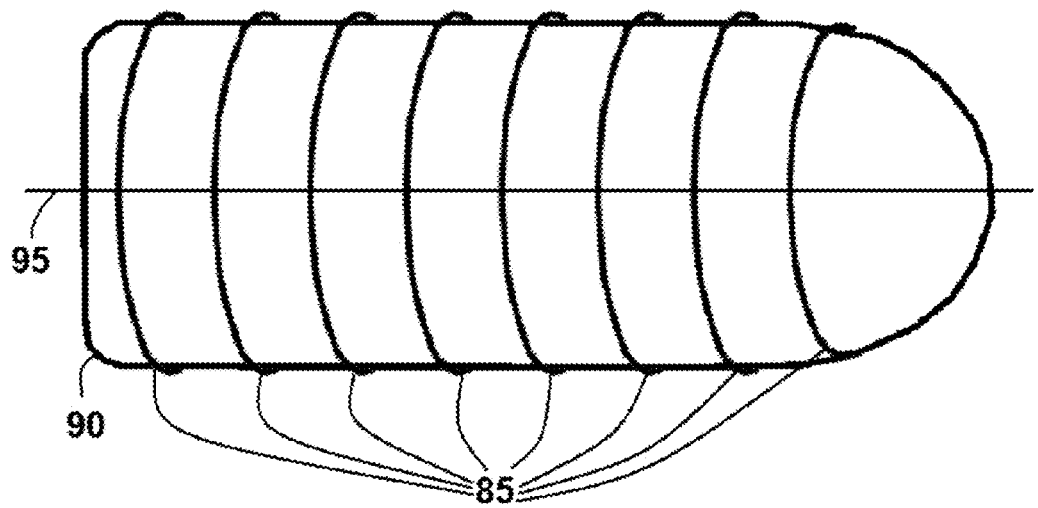
FIG. 8 illustrates a perspective view of an exemplary embodiment of a retention member and a plurality of detectors, according to the present disclosure.

In still other embodiments, detectors 100 may be configured in a planar arrangement in a flexible material that can be wrapped around a retention member. As shown in FIGS. 5 and 6, detectors 100 can be inserted into channels 85 of a cover 80, which may comprise a material that is flexible enough to be wrapped around a retention member in various configurations. For example, as shown in FIG. 7, cover 80 may be wrapped around retention member 90 so that channels 85 (as well as detectors 100, not visible in FIG. 7) form a spiral or helical configuration along an a primary axis 95 of retention member 90. In addition, as shown in FIG. 8, cover 80 may be wrapped around retention member 90 so that channels 85 form an annular arrangement around axis 95 of retention member 90. In certain embodiments, cover 80 is configured so that it does not wrap completely around retention member 90, but instead wraps partially around the circumference of retention member 90.

Figure 9:
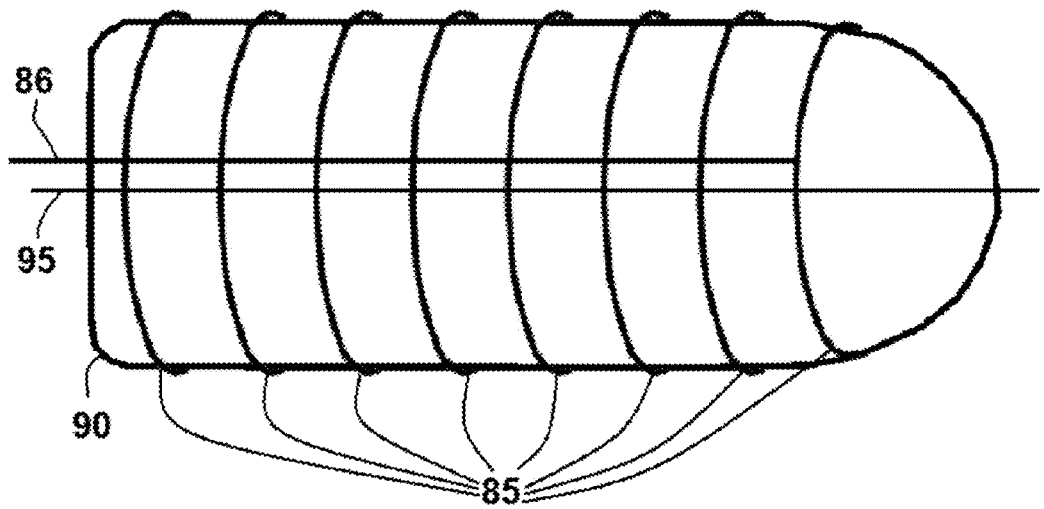
FIG. 9 illustrates a perspective view of an exemplary embodiment of a retention member and a plurality of detectors, according to the present disclosure.

Referring now to FIG. 9, in still other embodiments a portion of the channels 85 can be arranged to form an annular arrangement along retention member 90, while one or more detectors are arranged orthogonal to the annular detectors 100. As shown in FIG. 9, a channel 86 is arranged orthogonal to channels 85. Channel 86 may comprise a detector that forms a wavelength shifting member. The detector in channel 86 can absorb the scintillation light produced in the annular scintillating detectors in channels 85 and re-emits light at higher wavelength isotropically and proportionally to the absorbed scintillation light. The wavelength shifting detector can allow a signal to be obtained from the several annular detectors at the same time. In this embodiment, each annular detector is optically coupled the wavelength shifting member at their intersection cross-section.

Figure 10:
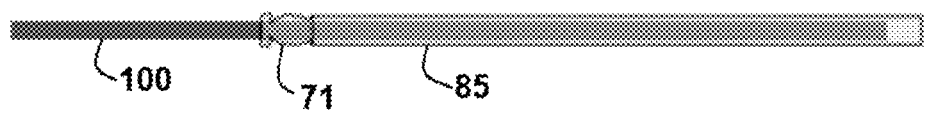
FIG. 10 illustrates a side view of an exemplary embodiment of a locking member and a detector, according to the present disclosure.
Figure 11:
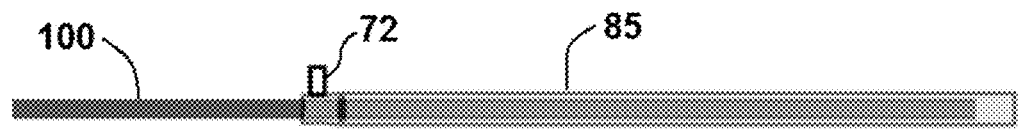
FIG. 11 illustrates a side view of an exemplary embodiment of a locking member and a detector, according to the present disclosure.

In exemplary embodiments, the detectors may be held in place by one of a number of different mechanisms. For example, as shown in FIG. 10, a locking member 71 provides a pressure-based locking mechanism similar to a rubber band or o-ring. Referring now to FIG. 11, in other embodiments, a locking member 72 may utilize air pressure to hold a detector in a channel. For example, locking member 72 may comprise an inflatable element that expands as air pressure is increased, allowing locking member 72 to retain the detector in the desired location within the channel.

Figure 12:
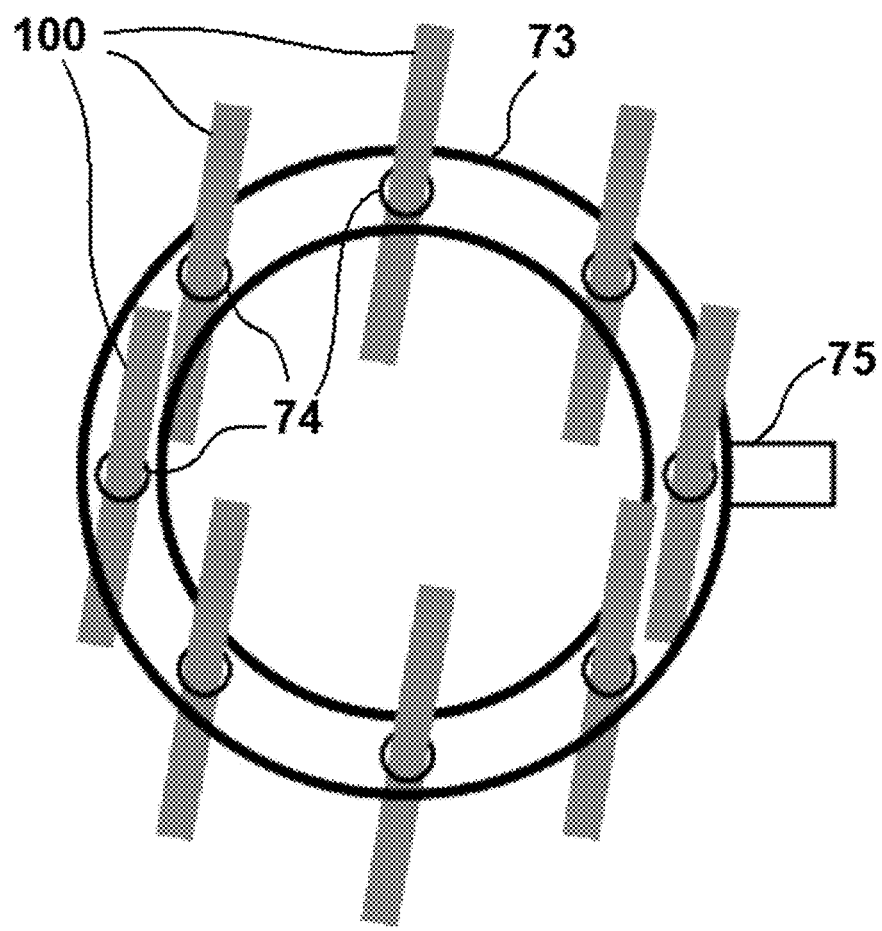
FIG. 12 illustrates a perspective view of an exemplary embodiment of a locking member and a plurality of detectors, according to the present disclosure.

Referring now to FIG. 12, still other exemplary embodiments may comprise a single locking member 73 that can be used to retain multiple detectors 100 in a desired location. In this embodiment, locking member 73 comprises a valve mechanism 75 that can be operated to lock the detectors in the desired location. In each of the embodiments incorporating a locking mechanism to hold the detectors in place, the locking mechanism should be configured so that it does not exert a force on the detector sufficient to deform the outer surface of the detector and potentially cause a reduction in the signal provided by the detector.

Figure 13:
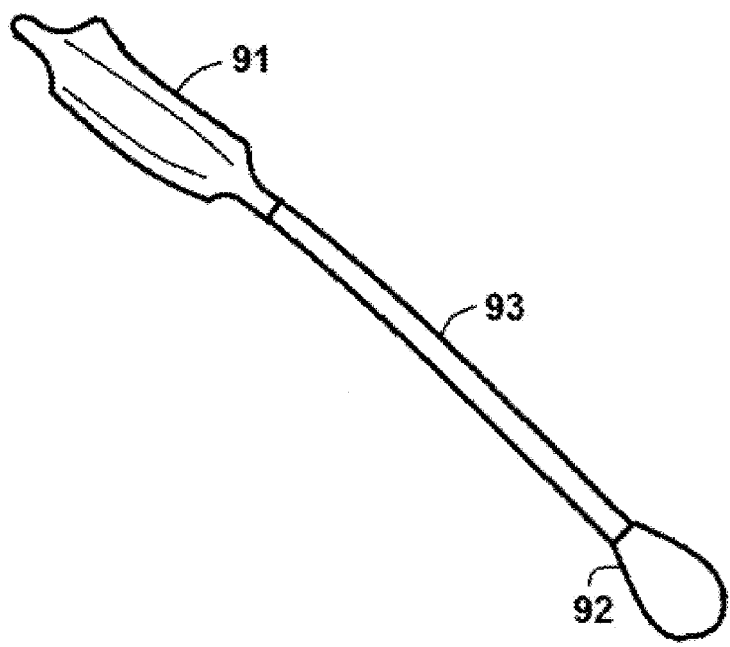
FIG. 13 illustrates a perspective view of an exemplary embodiment of a retention member, according to the present disclosure.
Figure 14:
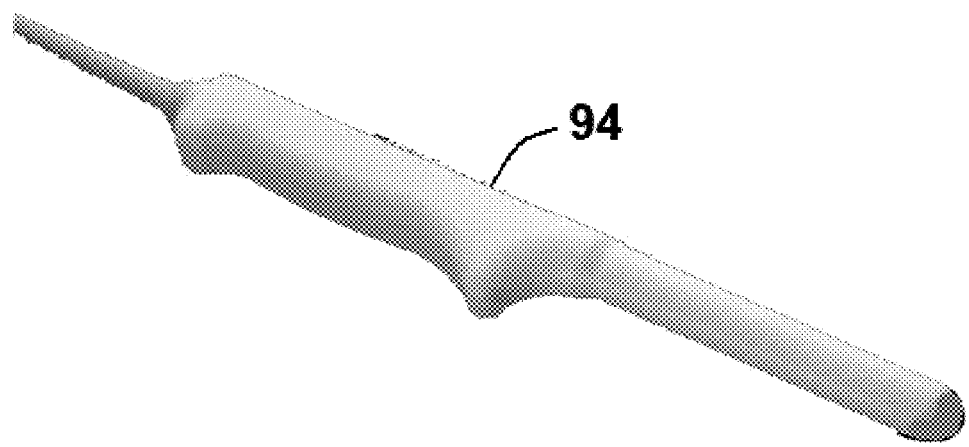
FIG. 14 illustrates a perspective view of an exemplary embodiment of a retention member, according to the present disclosure.

As previously described, in certain embodiments detectors can be coupled to a cover that is used to cover a retention member. Referring now to FIG. 13, in certain embodiments the retention member may be a rectal balloon 91. In the embodiment shown in FIG. 13, rectal balloon 91 is coupled to an inflation member 92 via a conduit 93. As known to those skilled in the art, rectal balloon 91 can be inflated after insertion into the patient by repeatedly grasping and releasing inflation member 92. In other embodiments a cover incorporating detectors may be placed over other types of inflatable devices, including for example, a Foley catheter. In still other embodiments, a cover incorporating detectors may be placed over a retention member that is not inflatable. For example, such a cover may be placed over an ultrasonic probe 94, as shown in FIG. 14. In other embodiments, such a cover may be placed over enema tips or other non-inflatable devices.

Figure 15A:
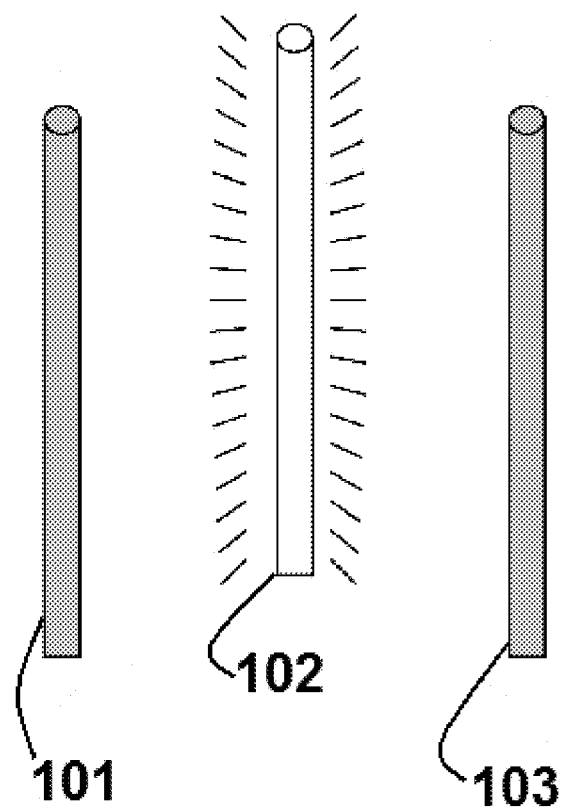
FIG. 15A illustrates a perspective view of an exemplary embodiment of a plurality of detectors.
Figure 15B:
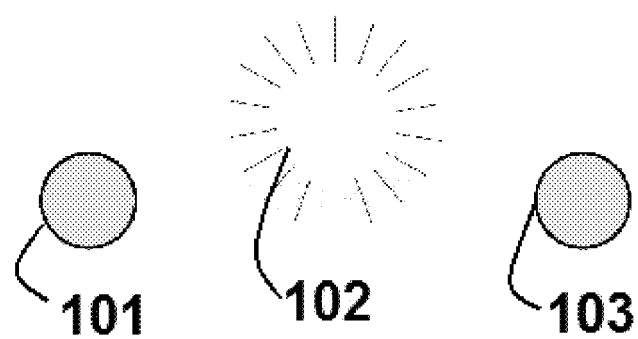
FIG. 15B illustrates an end view of an exemplary embodiment of a plurality of detectors.

The various types of retention members described above (as well as other specific configurations not explicitly mentioned in this disclosure) can be used to place one or more detectors 100 in a desired location within a patient. By monitoring the response of the individual detectors during radiation treatment, the level and area of radiation exposure may be determined. FIG. 15A depicts a partial side view of adjacent detectors 101, 102, and 103, while FIG. 15B depicts an end view of the same detectors. During initial stages of radiation exposure, only detector 102 may be exposed to sufficient levels of radiation to cause a response (e.g., an emission of light). As shown in FIGS. 15A and 15B, adjacent detectors 101 and 103 have not produced a response. Therefore an operator can determine that the area proximal to detector 102 has been exposed to a certain threshold level of radiation, while the areas proximal to detectors 101 and 103 have not been exposed to the same levels of radiation.

Figure 16A:
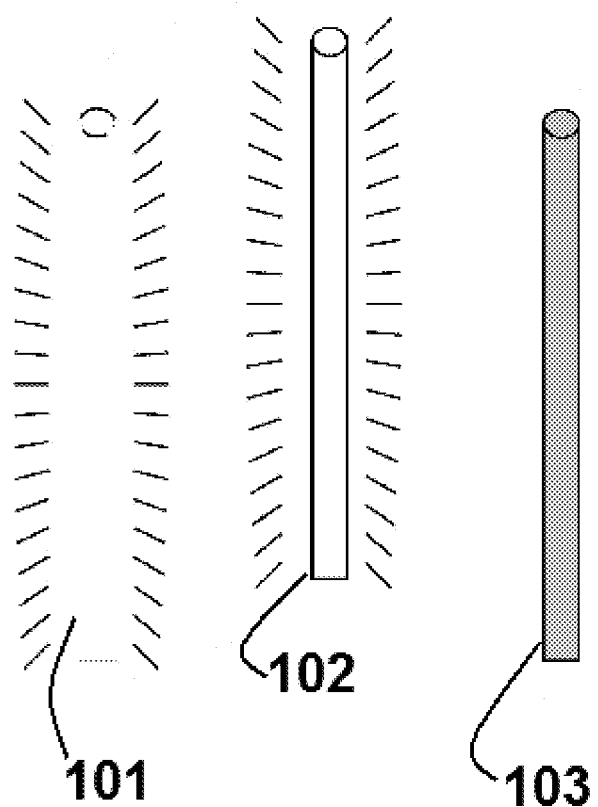
FIG. 16A illustrates a perspective view of an exemplary embodiment of a plurality of detectors.
Figure 16B:
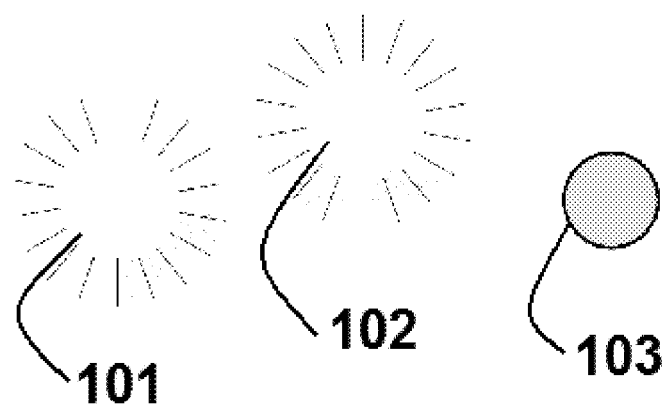
FIG. 16B illustrates an end view of an exemplary embodiment of a plurality of detectors.
Figure 17A:
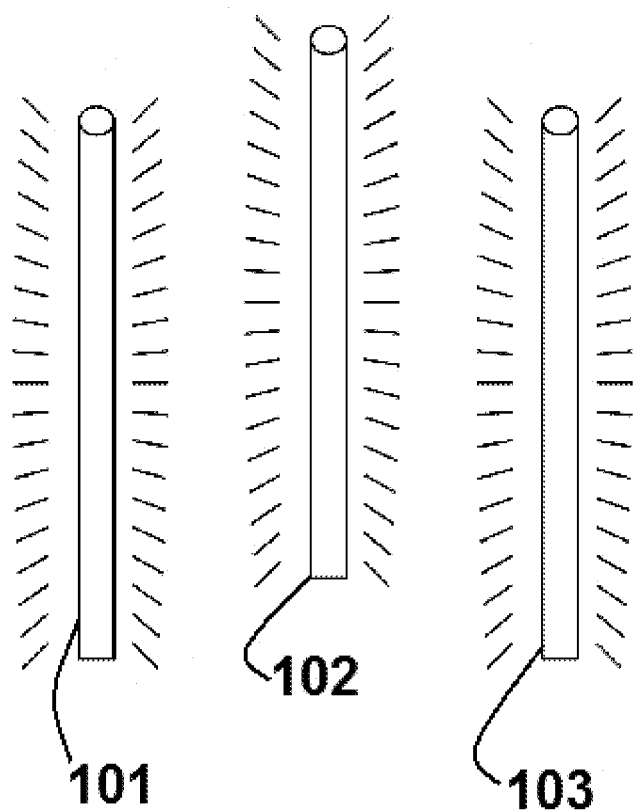
FIG. 17A illustrates a perspective view of an exemplary embodiment of a plurality of detectors.
Figure 17B:
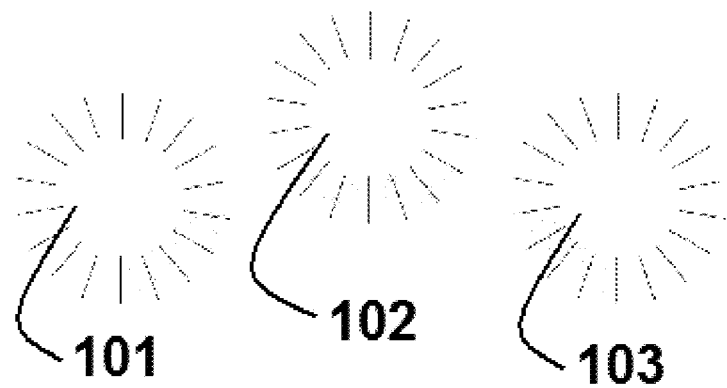
FIG. 17B illustrates an end view of an exemplary embodiment of a plurality of detectors.

As shown in FIGS. 16A and 16B, when the radiation level to the area proximal to detector 101 (e.g., the area left of detector 102) is increased, detector 101 will also produce a response. Similarly, as shown in FIGS. 17A and 17B, when the radiation level to the area proximal to detector 103 (e.g., the area to the right of detector 102) is increased, detector 103 will also produce a response. By individually tracking the responses of each detector, a user can accurately and precisely monitor the area and levels of radiation exposure. This can allow the user to better control the radiation exposure to the patient and provide radiation to the desired areas while minimizing radiation exposure to areas in which it is not desired. For example, a detection system may include a feature to automatically stop exposing the patient to radiation when certain criteria are met. In certain embodiments, the radiation exposure may be ceased when a certain number of probes detect a specific threshold of radiation levels. In other embodiments, the radiation exposure may be ceased when one or multiple probes in certain locations detect a specific threshold of radiation level.

Furthermore, exemplary embodiments of the detection systems are capable of monitoring radiation levels in real-time, e.g. the system is capable of producing a response without a significant delay from the time the detector is exposed to a threshold level of radiation. This can also allow a user to more precisely control the radiation dosage levels to which a patient is exposed. In specific, non-limiting examples the detection system is configured to provide a response in less than 1 second. In other non-limiting examples, the detection system is configured to provide a response in less than 2, 3, 4, 5, 6, 7, 8, 9 or 10 seconds.

Figure 18:
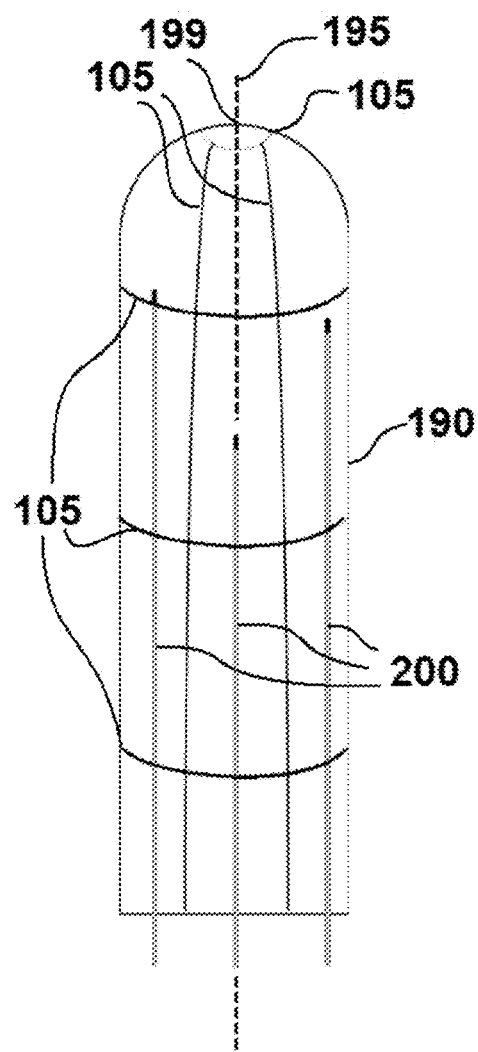
FIG. 18 illustrates a side view of an exemplary embodiment of a retention member and a plurality of detectors and radiopaque markers, according to the present disclosure.
Figure 19:
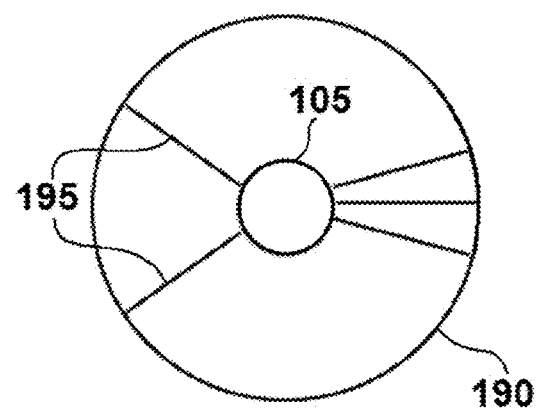
FIG. 19 illustrates an end view of an the exemplary embodiment of FIG. 18.

Referring now to FIGS. 18-19, in certain embodiments a retention member 190 may be configured as a flexible rectal or vaginal dilator. In specific embodiments, retention member 190 may be a rectal or vaginal dilator comprised of silicone. In the embodiment shown, a plurality of radiopaque markers 105 may be coupled (e.g., embedded) to retention member 190. Radiopaque markers 105 are opaque to radiation and are therefore visible during radiation treatment (e.g., when retention member 190 is inserted in vivo and the area proximal to retention member 190 is exposed to radiation). In specific embodiments, radiopaque markers 105 may be arranged so that they extend along the primary or longitudinal axis 195 of retention member 190 and to a distal end 199 as shown in FIG. 18. In addition, radiopaque markers 105 may be configured so that they are perpendicular to longitudinal axis 195 of retention member 190 as shown in FIG. 19. In certain embodiments, radiopaque markers 105 are arranged asymmetrically to allow the rotational position of retention member 190 to be determined. Radiopaque markers 105 can therefore allow the longitudinal and rotational position of retention member 199 to be determined during and after insertion into a patient.

In addition to radiopaque markers 105, retention member 190 also comprises a plurality of detectors 200 configured to detect radiation. In specific embodiments, detectors 200 comprise a scintillating material configured to emit light when irradiated. In certain embodiments, detectors 200 may be configured as one or more scintillating fibers. As shown in FIG. 18, detectors 200 may extend to different lengths along retention member 190. For example, detectors 200 may be arranged generally parallel to longitudinal axis 195 and terminate at different distances from distal end 199 of retention member 190. This arrangement can allow the dosage level to be determined at various locations along retention member 190.

Figure 20:
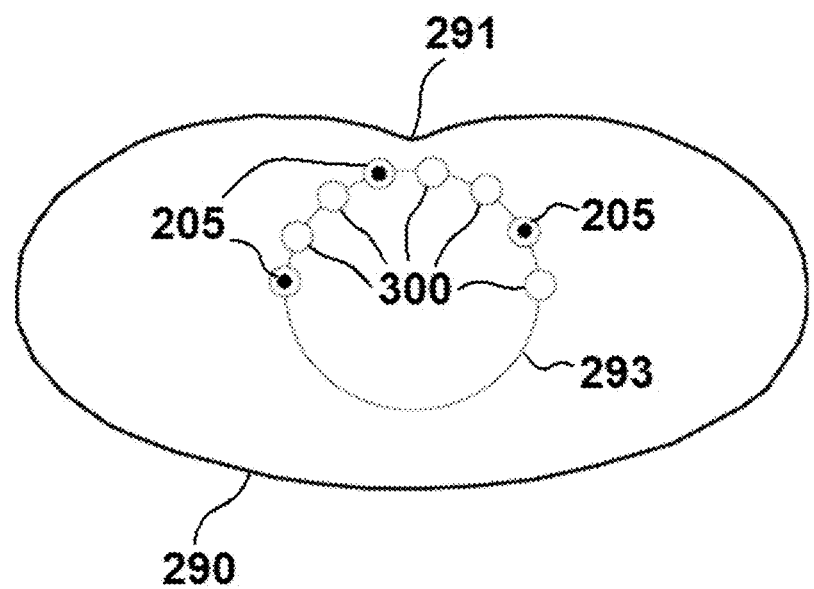
FIG. 20 illustrates an end view of an exemplary embodiment of a retention member and a plurality of detectors and radiopaque markers, according to the present disclosure.

Referring now to FIG. 20, a retention member 290 may be configured as an inflatable rectal balloon whose shape conforms to the prostate. In specific embodiments, retention member 290 may be configured as having a cross-section that is generally elliptical and has a greater width than height (when viewed in the position shown in FIG. 20) and includes an indentation 291 located along the wider portion of retention member 290. In certain embodiments, retention member 290 may comprise an insertion rod 293 coupled to a plurality of radiopaque markers 205 and a plurality of detectors 300 (including, for example, detectors comprising scintillating material). Similar to previously-described embodiments, the spatial relationship between radiopaque markers 205, detectors 300, and features (e.g., an end) of retention member 290 are known prior to insertion into a patient. This allows a user to determine the location of retention member 290 and the level of radiation dosage provided to a patient after retention member 290 has been inserted into a patient's rectum and the region proximal to the prostate has been exposed to radiation.

Scintillating fibers with radiopaque markers are attached to the insertion rod within the balloon. The radiopaque markers are placed at a known distance from the scintillating fiber tip and are used to localize the position of the detector. The scintillating fibers are placed at various heights along the insertion rod.

Figure 21:
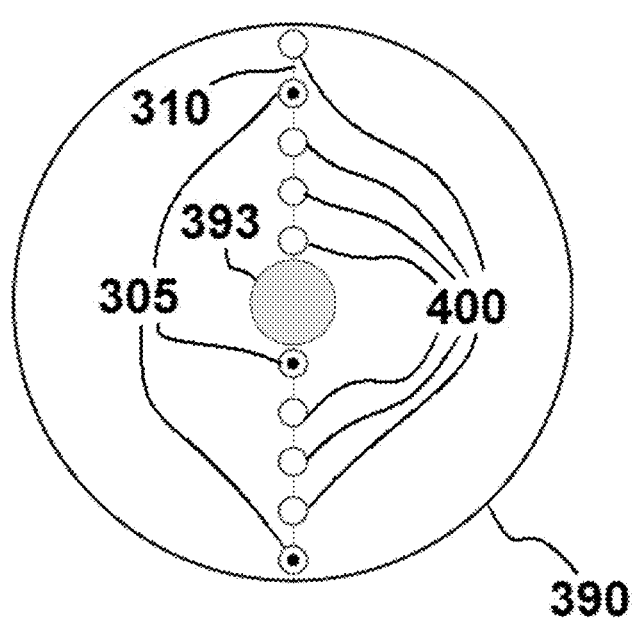
FIG. 21 illustrates an end view of an exemplary embodiment of a retention member and a plurality of detectors and radiopaque markers, according to the present disclosure.

Referring now to FIG. 21, a retention member 390 may be configured as an inflatable rectal balloon with an insertion rod 393. In this exemplary embodiment, retention member 390 comprises a plurality of radiopaque markers 305 and detectors 400 that function generally equivalent to those in previously-described embodiments. In this embodiment, retention member 390 comprises a flexible coupling member 310 that extends across retention member 390 and is coupled to radiopaque markers 305 and detectors 400.

In exemplary embodiments, flexible coupling member 310 can expand or contract as the diameter of retention member 390 is altered. For example, retention member 390 may be deflated prior to insertion within a patient, and insertion rod 393 can be used to insert retention member 390 into the patient's rectum. When retention member 390 is located in the desired position, retention member 390 can be expanded (e.g., inflated) so that the outer diameter of retention member 390 is increased. As the diameter of retention member 390 is increased, flexible coupling member 310 expands and increases the distance between individual radiopaque markers 305 and detectors 400.

Figure 22:
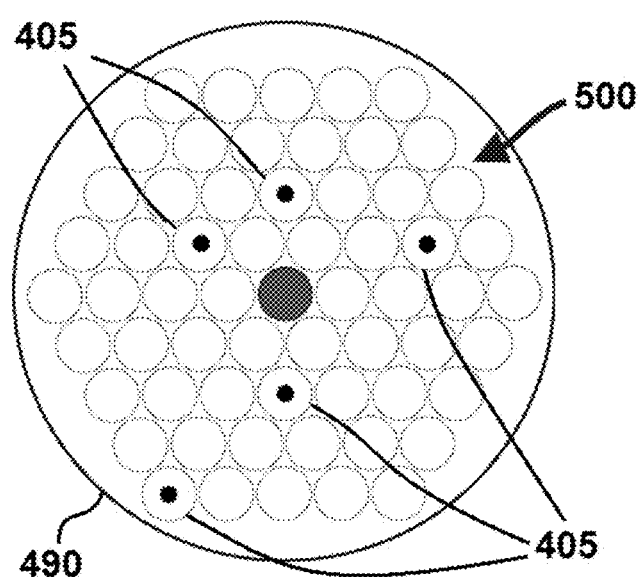
FIG. 22 illustrates an end view of an exemplary embodiment of a retention member and a plurality of detectors and radiopaque markers, according to the present disclosure.

Referring now to FIG. 22, a retention member 490 is configured as a rigid rectal probe. In this embodiments, a plurality of radiopaque makers 405 and detectors 500 are located within retention member 490. In the exemplary embodiment shown, detectors 500 are configured as a closely packed unit within retention member 490. In certain embodiments, retention member 490 may comprise approximately 10, 15, 20, 25, 30, 35, 40, 45 or 50 detectors 500.

All of the apparatus and/or methods disclosed and claimed herein can be made and executed without undue experimentation in light of the present disclosure. While the apparatus and methods of this invention have been described in terms of preferred embodiments, it will be apparent to those of skill in the art that variations may be applied to the apparatus and/or methods and in the steps or in the sequence of steps of the method described herein without departing from the concept, spirit and scope of the invention.

REFERENCES

The following references, to the extent that they provide exemplary procedural or other details supplementary to those set forth herein, are specifically incorporated herein by reference.
U.S. Patent Publn. 2007/0129693
U.S. Patent Publn. 2007/0114425
Aznar et al., *Phys. Med. Biol.*, 49:1655-1669, 2005.
Aznar et al., *Rad. Pro. Dos.*, 114:444-449, 2005.
Beddar et al., *Med. Phys.*, 21:1075-1079, 1994.
Beddar et al., *Med. Phys.*, 32:1265-1269, 2005.
Beddar et al., *Phys. Med. Biol.*, 37:1883-1900, 1992.
Beddar et al., *Phys. Med. Biol.*, 37:1901-1913, 1992.
Beddar et al., *Phys. Med. Biol.*, 50:141-149, 2005.
Ramaseshan et al., *Phys. Med. Biol.*, 49:4031-4048, 2004.
Scarantino et al., *Med. Phys.*, 31:2658-2671, 2004.
Soubra and Cygler, *Med. Phys.*, 21:567-572, 1994.

The invention claimed is:

1. A method of measuring radiation levels in real time during radiation therapy of a prostate, the method comprising:
   (a) inserting a rectal balloon into a rectum of a male patient having prostate cancer;
      (i) said rectal balloon having an external shape that conforms to a prostate, wherein said rectal balloon has a cross-section that is generally elliptical having a greater width than height when viewed from a first end of said rectal balloon, and wherein said rectal balloon has an indentation along its width;
      (ii) said rectal balloon coupled to a dosimeter comprising a plastic scintillating material coupled to an optical guide;
      (iii) said indentation of said rectal balloon extending axially from the first end of said rectal balloon; and
      (iv) said indentation extending inward toward said dosimeter;
   (b) inflating said rectal balloon;
   (c) coupling said dosimeter to a photodetector coupled to a data analyzer;
   (d) initiating a radiation therapy of said prostate;
   (e) calculating a level of radiation at said prostate based on the amount of light detected by said photodetector; and
   (f) stopping said radiation therapy when said calculated level of radiation is equal to a predetermined level of radiation.

2. The method of claim 1, wherein said balloon comprises a channel and said dosimeter is inside said channel.

3. The method of claim 2, wherein said rectal balloon comprises one or more radiopaque markers, the method further comprising:
   (a) visualizing said one or more radiopaque markers; and
   (b) positioning said rectal balloon based on said visualization so that said rectal balloon is in a desired location.

4. The method of claim 2, wherein said rectal balloon comprises radiopaque markers asymmetrically arranged on said rectal balloon, the method further comprising:
   (a) determining the position of said radiopaque markers; and
   (b) positioning said rectal balloon until said rectal balloon is in a desired location based on said position of said radiopaque markers.

5. The method of claim 1 wherein said radiation therapy is radiation beam therapy.

6. The method of claim 1, wherein said rectal balloon comprises one or more radiopaque markers, the method further comprising:
   (a) visualizing said one or more radiopaque markers; and
   (b) positioning said rectal balloon based on said visualization so that said rectal balloon is in a desired location.

7. A device for in vivo real time dosimetry during radiation therapy, said device comprising:
   (a) an inflatable rectal balloon fluidly coupled to a conduit for inflating said balloon;
   (b) said balloon having an external shape that conforms to a prostate, wherein said rectal balloon has a cross-section that is generally elliptical having a greater width than height when viewed from a first end of said rectal balloon, and has an indentation along its width;
   (c) said rectal balloon comprising a channel thereon, said channel containing a real time dosimeter;
   (d) said indentation of said rectal balloon extending axially from the first end of said rectal balloon; and
   (e) said indentation extending inward toward the real time dosimeter;
   (f) said real time dosimeter comprising a water equivalent plastic scintillator coupled to an optical fiber; and
   (g) wherein said real time dosimeter can monitor an in vivo dose of radiotherapy beams or brachytherapy in real time.

8. The rectal balloon of claim 7, said rectal balloon further comprising an indentation when inflated to conform said rectal balloon to a prostate when in use.

9. The rectal balloon of claim 7, wherein said real-time dosimeter comprises a plurality of plastic scintillators optically coupled to a plurality of optical fibers and wherein one or more of the optical fibers extend different lengths along said rectal balloon.

10. The rectal balloon of claim 7, wherein a plurality of channels contain a plurality of real-time dosimeters.

11. The rectal balloon of claim 7, further comprising one or more radiopaque markers on said rectal balloon.

12. The rectal balloon of claim 7, further comprising one or more radiopaque markers arranged asymmetrically on said rectal balloon.

13. The rectal balloon of claim 7, wherein said real time dosimeter is configured to be coupled to a photodetector.

* * * * *